US008837798B2

(12) United States Patent
Li et al.

(10) Patent No.: US 8,837,798 B2
(45) Date of Patent: Sep. 16, 2014

(54) SIGNAL AND IMAGE ANALYSIS METHOD AND ULTRASOUND IMAGING SYSTEM

(75) Inventors: Arvin Huang-Te Li, Chiayi (TW); Yio-Wha Shau, Taipei (TW); Yu-Ching Chang, Hsinchu (TW); Bai-Kuang Hwang, Hsinchu (TW); Min Shih, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 99 days.

(21) Appl. No.: 13/553,793

(22) Filed: Jul. 19, 2012

(65) Prior Publication Data

US 2013/0163839 A1    Jun. 27, 2013

(30) Foreign Application Priority Data

Dec. 27, 2011   (TW) .............................. 100148921 A

(51) Int. Cl.
  *G06K 9/00* (2006.01)
  *G06K 9/46* (2006.01)
(52) U.S. Cl.
  USPC .......................................... 382/131; 382/207
(58) Field of Classification Search
  CPC ...................... G06F 17/14; G06T 2207/10132
  USPC ............................ 382/131; 702/2, 4, 189, 194
  See application file for complete search history.

(56) References Cited

U.S. PATENT DOCUMENTS

| | | | |
|---|---|---|---|
| 5,582,171 A | 12/1996 | Chornenky et al. | |
| 5,983,162 A * | 11/1999 | Huang | 702/4 |
| 6,068,599 A | 5/2000 | Saito et al. | |
| 6,311,130 B1 * | 10/2001 | Huang | 702/2 |
| 6,381,559 B1 * | 4/2002 | Huang | 702/194 |
| 6,423,006 B1 | 7/2002 | Banjanin | |
| 6,464,641 B1 | 10/2002 | Pan et al. | |
| 6,482,161 B1 | 11/2002 | Sumanaweera et al. | |
| 6,738,734 B1 * | 5/2004 | Huang | 702/194 |
| 6,862,558 B2 * | 3/2005 | Huang | 702/194 |

(Continued)

FOREIGN PATENT DOCUMENTS

| | | |
|---|---|---|
| CN | 1134808 | 11/1996 |
| CN | 101822548 | 9/2010 |

(Continued)

OTHER PUBLICATIONS

Tong et al. "Improved Synthetic Aperture Focusing Technique by Hilbert-Huang Transform for Imaging Defects Inside a Concrete Structure", IEE Transactions on Ultrasounds, vol. 57, No. 11, Nov. 2010.*

(Continued)

*Primary Examiner* — Amir Alavi
*Assistant Examiner* — Kenny Cese
(74) *Attorney, Agent, or Firm* — Jianq Chyun IP Office

(57) ABSTRACT

A time domain signal analysis method is provided. The signal analysis method includes the following steps. A signal to be analyzed is received. The signal to be analyzed is iteratively sifted by using Empirical Mode Decomposition (EMD) to extract at least one intrinsic function (IMF). A normalized Hilbert transform is performed on the IMF. The transformed IMF includes phase information. The transformed IMF is processed by means of phase processing to obtain the processed IMF including angular frequency information. The foregoing signal analysis method could be utilized in an ultrasound imaging system to identify image information of ultrasound images.

20 Claims, 4 Drawing Sheets

(56) References Cited

U.S. PATENT DOCUMENTS

| | | | |
|---|---|---|---|
| 6,901,353 B1* | 5/2005 | Huang | 702/189 |
| 7,464,006 B1* | 12/2008 | Huang | 702/190 |
| 7,930,014 B2 | 4/2011 | Huennekens et al. | |
| 7,941,298 B2* | 5/2011 | Huang et al. | 702/194 |
| 7,955,293 B2 | 6/2011 | Nita et al. | |
| 2006/0184021 A1 | 8/2006 | Kim et al. | |
| 2006/0184029 A1 | 8/2006 | Haim et al. | |
| 2006/0241465 A1 | 10/2006 | Huennekens et al. | |
| 2010/0113930 A1 | 5/2010 | Miyachi | |
| 2010/0207942 A1 | 8/2010 | Zhao | |
| 2010/0210946 A1 | 8/2010 | Harada et al. | |
| 2010/0234732 A1 | 9/2010 | Wrobel | |
| 2011/0044522 A1 | 2/2011 | Fancourt et al. | |
| 2011/0075912 A1 | 3/2011 | Rieber et al. | |
| 2011/0137175 A1 | 6/2011 | Hossack et al. | |

FOREIGN PATENT DOCUMENTS

| | | |
|---|---|---|
| CN | 101904753 | 12/2010 |
| TW | 594032 | 6/2004 |
| TW | I252929 | 4/2006 |
| TW | I268149 | 12/2006 |
| TW | 201023836 | 7/2010 |

OTHER PUBLICATIONS

Zhang et al. "The Removal of Wall Components in Doppler Ultrasound Signals by Using the Empirical Mode Decomposition Algorithm", IEEE Transactions on Biomedical Engineering, vol. 54, No. 9, Sep. 2007.*

Kamalov et al., "The significance of colour velocity and spectral Doppler ultrasound in the differentiation of liver tumours," European Journal of Ultrasound, Apr. 1998, pp. 101-108, vol. 7.

Guerrero et al., "Real-Time Vessel Segmentation and Tracking for Ultrasound Imaging Applications," IEEE Transactions on Medical Imaging, Aug. 2007, pp. 1079-1090, vol. 26, No. 8.

Office Action of China Counterpart Application, issued on May 30, 2014, p. 1-p. 10.

* cited by examiner

SIGNAL AND IMAGE ANALYSIS METHOD AND ULTRASOUND IMAGING SYSTEM

CROSS-REFERENCE TO RELATED APPLICATION

This application claims the priority benefit of Taiwan application serial no. 100148921, filed on Dec. 27, 2011. The entirety of the above-mentioned patent application is hereby incorporated by reference herein and made a part of this specification.

TECHNICAL FIELD

The technical field relates to a signal and image analysis method and an ultrasound imaging system.

BACKGROUND

Conventional ultrasound imaging has been widely applied in various domains such as industry, military, and medicine etc. When the ultrasound imaging system is applied in medical applications, it can be used to measure physiological characteristics of human tissues such as flow rates of blood in blood vessels, etc. Ultrasound energy is transmitted to a region of human tissue to be detected, and ultrasound energy reflected by said region is received. According to the reflected ultrasound energy, an ultrasound imaging system can display a two-dimensional ultrasound image of the region to be detected. However, regarding the detection of low flow rates of the blood in blood vessels or the diameters of smaller blood vessels, specific signal analysis methods are required to analyse the ultrasound energy reflected by the region to be detected, so as to obtain the related information.

According to the conventional signal analysis methods, the reflected ultrasound energy is analyzed in frequency domain. However, such frequency domain analysis methods have some shortcomings. In detail, according to the Doppler principle, when the ultrasound imaging system sends the ultrasound to a moving object in the region to be detected, for example, an erythrocyte in the blood vessel, a frequency of an echo signal reflected by the moving object is shifted, and the frequency shift is proportional to a component of the speed of the moving object along an ultrasound transmission direction. In a pulsed wave Doppler mode, a probe of the ultrasound imaging system sends a series of short pulses to the region to be detected, and the reflected signals received by the ultrasound imaging system can be represented as a two-dimensional data set, where one dimension represents a pulse sending index (i.e. a slow time axis), and another dimension represents a flying time (i.e. a fast time axis). The signals on the slow time axis carry the Doppler shift information. Therefore, the characteristic information of the moving object can be obtained by analyzing the phases of the signals on the slow time axis.

The conventional signal analysis method generally calculates a self-correlation function of two adjacent signals on slow time axis to estimate a phase shift, and accordingly calculates information of the moving object such as the speed, etc. However, according to the conventional signal analysis method, the signal on the slow time axis is processed by Fourier transform, that is, the signal analysis is performed in frequency domain. However, the conventional signal analysis method has following shortcomings. The Doppler signal tends to be interfered by low-frequency signals, for example, pulses of a vessel wall, heart pulses, breathing or involuntary movements. Such method has to use a high-pass filter (a wall filter) to filter the noises, so as to perform the subsequent analysis. It is not easy to design an ideal high-pass filter, so the complexity of the frequency domain analysis method is increased. The Fourier transform that serves as a core algorithm of frequency domain analysis method is essentially an integral transform, and once time domain signals are transformed, all of time-varying information are completely lost. Therefore, the conventional signal analysis method cannot provide specific instantaneous frequency information in an actual measurement.

SUMMARY

An embodiment of the disclosure provides a time domain signal analysis method, and the signal analysis method includes the following steps: (a) a signal to be analyzed is received. (b) the signal to be analyzed is iteratively sifted by using empirical mode decomposition (EMD) to extract at least one intrinsic mode function (IMF). (c) a normalized Hilbert transform is performed on the IMF, where the transformed IMF comprises phase information. (d) the transformed IMF is processed by means of phase processing to obtain the processed IMF comprising angular frequency information.

Another embodiment of the disclosure provides a method for analyzing an ultrasound image, which is adapted to an ultrasound imaging system, and includes following steps: (a) a signal to be analyzed is received. (b) the signal to be analyzed is iteratively sifted by using empirical mode decomposition (EMD) to extract at least one intrinsic mode function (IMF). (c) a normalized Hilbert transform is performed on the IMF, where the transformed IMF comprises phase information. (d) the transformed IMF is processed by means of phase processing to obtain the processed IMF including angular frequency information. (e) the processed IMF is compared to an ultrasound image related to the signal to be analyzed (for example, by overlaying the plot of the processed IMF on said ultrasound image) to identify image information of the ultrasound image.

Another embodiment of the disclosure provides an ultrasound imaging system including a signal transceiving module, a signal processing module and an image display module. The signal transceiving module receives a signal to be analyzed. The signal processing module iteratively sifts the signal to be analyzed by using empirical mode decomposition (EMD) to extract at least one intrinsic mode function (IMF). The signal processing module performs a normalized Hilbert transform on the IMF, where the transformed IMF comprises phase information. The signal processing module processes the transformed IMF by means of phase processing to obtain the processed IMF comprising angular frequency information. The signal processing module compares the processed IMF to an ultrasound image related to the signal to be analyzed to identify image information of the ultrasound image. The display module displays the ultrasound image corresponding to a region to be detected according to a processing result of the signal to be analyzed processed by the signal processing module.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1:
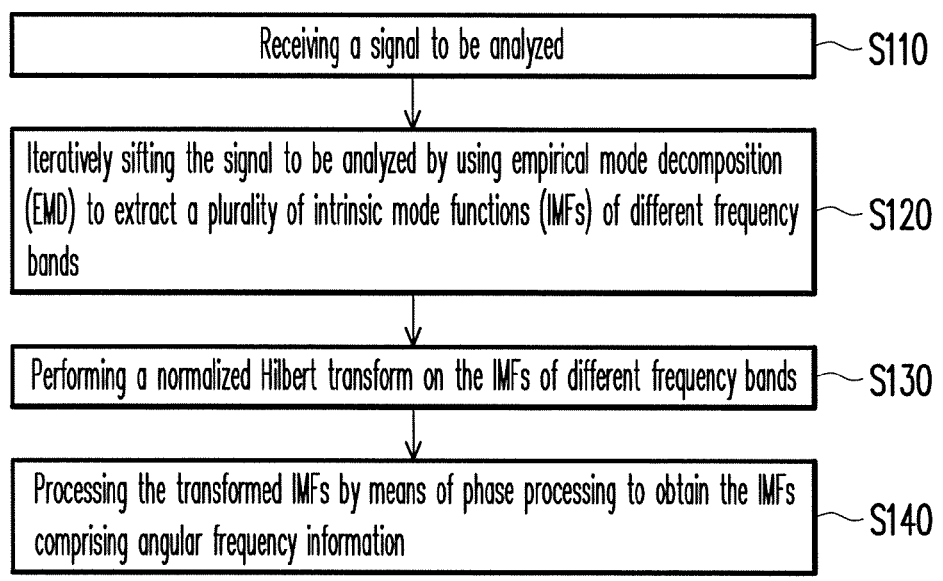
FIG. 1 is a flowchart illustrating a signal analysis method according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a flowchart illustrating a signal analysis method according to an embodiment of the disclosure. Referring to FIG. 1, the signal analysis method of the present embodiment processes signals in time domain to obtain time-varying frequency information. First, in step S110, a signal to be analyzed is received. The signal to be analyzed, for example, comprises a slow time axis signal reflected by a moving object in a region to be detected, which contains Doppler shift information. Then, in step S120, the signal to be analyzed is iteratively sifted by using empirical mode decomposition (EMD) to extract a plurality of intrinsic mode functions (IMFs) of different frequency bands. Patents US20100092028A1, U.S. Pat. No. 6,901,353B1, etc. can be referred for the EMD method. The decomposed results of such step comprise at least one IMF. In the present embodiment, if image information of the moving object can be obtained by analysis according to the at least one IMF, the disclosure is not limited to decompose a plurality of the IMFs of different frequency bands. In step S130, a normalized Hilbert transform is performed on the IMFs of different frequency bands, where each of the transformed IMFs comprises phase information. Then, in step S140, the transformed IMFs are processed by means of phase processing to obtain each of the IMFs including angular frequency information.

In the present embodiment, the phase processing means of the step S140 includes filtering noises such as surges in the angular frequency information in collaboration with curve fitting, i.e. filtering a component of angular frequency information to obtain stable angular frequency information. In detail, the phase processing means of the present embodiment includes differentiating the phase information of each of the IMFs to obtain the corresponding angular frequency information. Namely, assuming the phase information of each of the IMFs is $\phi$, and the angular frequency information is $\omega$, according to the phase processing means, the first order time derivative of the phase information $\phi$ of each of the IMFs is taken to obtain the angular frequency information $\omega = d\phi/dt$. Then, a part of components such as surges in the angular frequency information $\omega$ is filtered by using the curve fitting.

In brief, the signal analysis method of the present embodiment directly analyzes the slow time axis signal reflected by the region to be detected, by which the EMD is first performed on the slow time axis signal, and then the normalized Hilbert transform is performed to trim envelopes of the obtained IMFs, so as to directly obtain the phase information of each of the IMFs to calculate the angular frequency information thereof.

Moreover, in an embodiment, the signal analysis method further includes comparing the obtained IMF with a two-dimensional image related to the signal to be analyzed (for example, by overlaying the plot of said obtained IMF on said two-dimensional image) to identify image information of the two-dimensional image, where the image information includes a position, a size and a moving speed of the moving object. Since the signal analysis method of the present embodiment is a time domain approach, an analysis result thereof comprises time-varying frequency information, by which an actual measurement circumstance of the region to be detected is opportunely learned.

The signal analysis method of the present embodiment can be widely used to analyze the IMFs with envelopes trimmed by the Hilbert transform, and the phase processing means is used to obtain the stable angular frequency information. The signal analysis method is not limited to any type of signal detecting and processing system. In order to fully convey the spirit of the disclosure, an exemplary embodiment of applying the signal analysis method of the present embodiment in an ultrasound imaging system is described in detail below with reference to figures.

Figure 2:
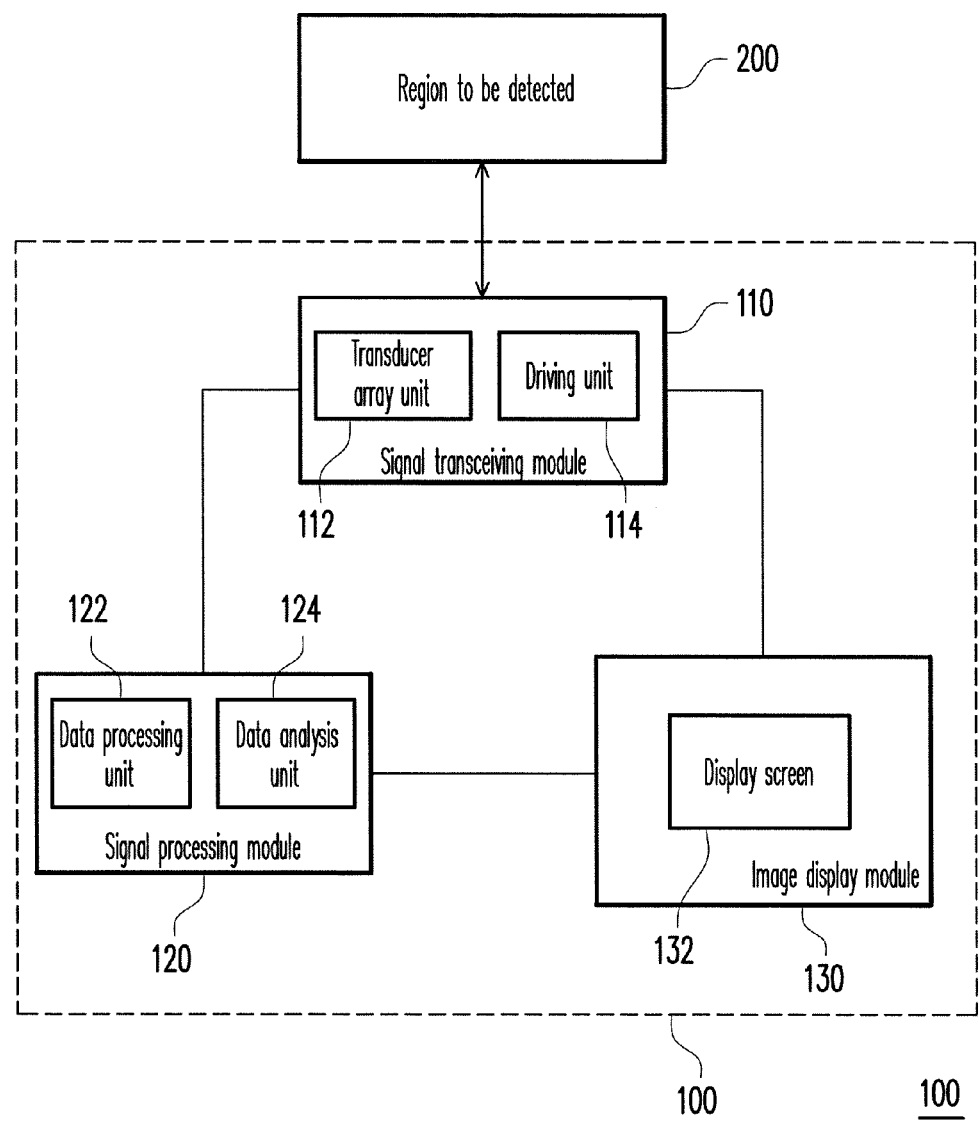
FIG. 2 is a block schematic diagram of an ultrasound imaging system according to an embodiment of the disclosure.

FIG. 2 is a block schematic diagram of an ultrasound imaging system according to an embodiment of the disclosure. Referring to FIG. 2, the ultrasound imaging system 100 of the present embodiment includes a signal transceiving module 110, a signal processing module 120 and an image display module 130. The signal transceiving module 110 includes a transducer array unit 112 and a driving unit 114. Here, the signal transceiving module, for example, includes an ultrasound probe at a front-end of the ultrasound imaging system 100. In the present embodiment, the driving unit 114 is used for providing a driving signal to transducers in the transducer array unit 112 to trigger each of the transducers to transmit an ultrasound signal to a region 200 to be detected. The transducer array unit 112 generates ultrasound signals after being triggered, and transmits the ultrasound signals to the region 200 to be detected. The region 200 to be detected is generally a tissue region of an organism or a transmission medium thereof (for example, a human/animal tissue or a transmission medium thereof), and in the present embodiment, the region 200 to be detected is, for example, a blood vessel with blood flowing therein. Then, an ultrasound reflected wave reflected by the region 200 to be detected is again received by the transducer array unit 112, and the post signal processing module 120 obtains a raw signal of the region to be detected, i.e. the signal to be analyzed.

In the present embodiment, after the transducer array unit 112 receives the reflected wave reflected by the region 200 to be detected, the transducer array unit 112 can convert the reflected analog wave signal into a digital signal. In other words, the transducer array unit 112 may further include an analog-to-digital converter, which is used for converting the reflected analog wave signal into digital signal, though the disclosure is not limited thereto. In other embodiments, the analog-to-digital conversion function can also be implemented by a circuit in internal of the driving unit 114, or implemented by an interface circuit between the signal transceiving module 110 and the signal processing module 120, which is not limited by the disclosure.

In the present embodiment, the signal processing module 120 includes a data processing unit 122, a data analysis unit 124. After the signal to be analyzed is received, the data processing unit 122 performs beamforming and focusing procedures on the signal to be analyzed. As described above, the transducers in the transducer array unit 112 are used to receive the reflected wave reflected by the region 200 to be detected. Regarding each of the transducers, a delay time thereof is different, so that a beamforming circuit is required to separately delay the image signal of each of the reflected waves. Therefore, the processing unit 122 includes a beamforming circuit to suitably introduce a differential delay to each of the received signals, so as to dynamically focus the signal to produce an accurate two-dimensional ultrasound image of the region to be detected.

Then, the signal processing module 122 converts the beamformed image into rectangular coordinates from polar coordinates to obtained a transformed image that uses rectangular coordinates to represent image intensities. Then, the data processing unit 122 converts the format of the beamformed image to facilitate the image display module 130 displaying the beamformed image on a display screen 132. In the present embodiment, the two-dimensional ultrasound image is obtained by the ultrasound imaging system 100 by detecting the region 200 to be detected under a B-scan mode.

On the other hand, in order to further identify the image information of the ultrasound image, the data analysis unit 124 performs the EMD on the signal to be analyzed that is reflected by the region 200 to be detected according to the signal analysis method of FIG. 1. Then, the data analysis unit 124 trims the envelope of IMF of the signal to be analyzed according to Hilbert transform, so as to directly obtain the phase information of each of IMFs in time domain by using the aforementioned phase processing means to calculate the angular frequency information thereof. Then, the data analysis unit 124 compares each of the processed IMFs to the ultrasound image of the signal to be analyzed, so as to identify image information of the ultrasound image. Here, the signal to be analyzed is obtained by the ultrasound imaging system 100 by detecting the region 200 to be detected under an A-scan mode. The image information of the ultrasound image, for example, includes a position, a size and a flow rate of blood in a blood vessel of a tissue of an organism (for example, human, animal, etc.).

Moreover, since those skilled in the art can learn enough instructions and recommendations of the ultrasound image analysis method of the disclosure from the descriptions of the embodiments of FIG. 1 and FIG. 2, detailed descriptions thereof are not repeated. On the other hand, the ultrasound image analysis method of the disclosure can be implemented by software or a field programmable gate array (FPGA) chip or other software or hardware approaches, which is not limited by the disclosure.

Figure 3A:
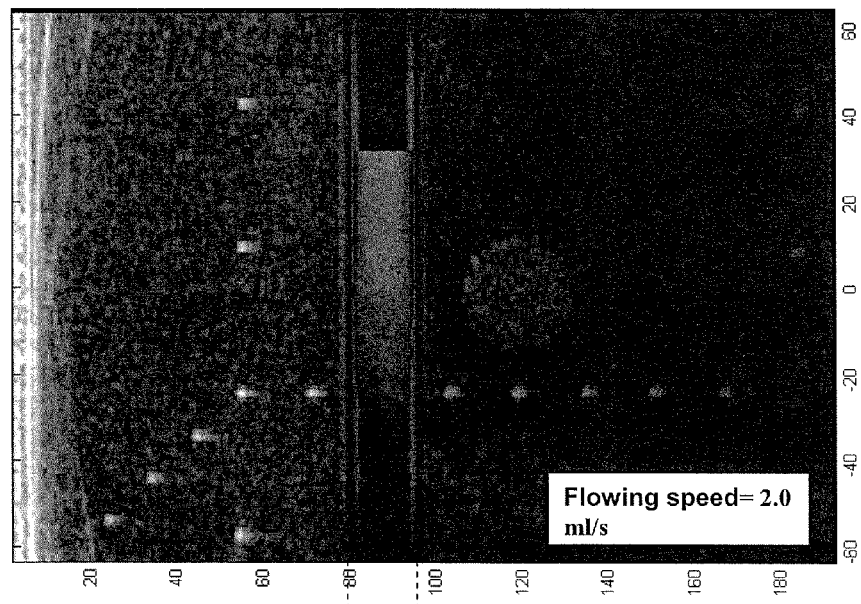
FIG. 3A is an ultrasound image of a phantom according to an embodiment of the disclosure.
Figure 3B:
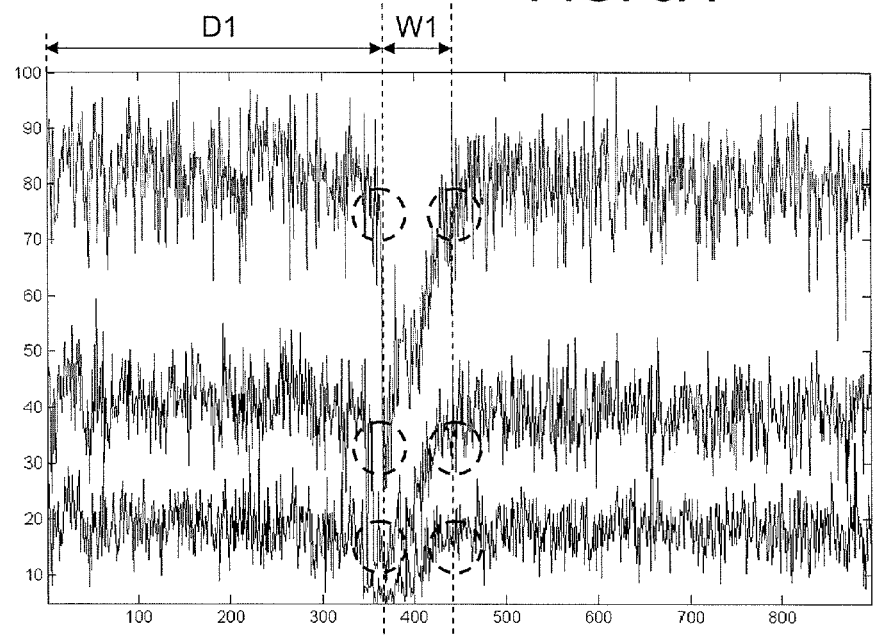
FIG. 3B is an intrinsic mode function (IMF) of a signal to be analyzed of the phantom of FIG. 3A.

FIG. 3A is an ultrasound image of a phantom according to an embodiment of the disclosure. FIG. 3B is an IMF of the signal to be analyzed of the phantom of FIG. 3A. The horizontal axis of FIG. 3A represents the depth of the phantom, and the vertical axis represents the horizontal position of the phantom. The horizontal axis of FIG. 3B represents the horizontal position of the phantom, and the vertical axis represents the normalized IMF intensity of each frequency band of the phantom. Referring to FIG. 3A and FIG. 3B, the ultrasound image of the phantom of FIG. 3A is, for example, obtained by the ultrasound imaging system 100 of FIG. 2 by detecting the region 200 to be detected under the B-scan mode, where the phantom is a soft tissue disposed in the region 200 to be detected that can be used to simulate a living body, which is adapted to ultrasound imaging of in vitro experiment. In FIG. 3A, the ultrasound probe of the ultrasound imaging system 100 sends ultrasound signals to the phantom of the region to be detected to detect a two-dimensional ultrasound image.

The IMFs of different frequency bands shown in FIG. 3B are IMFs obtained according to the signal analysis method of FIG. 1. As described above, the signal analysis method can be used to directly process each of the IMFs in the time domain to filter noises such as signal surges, etc. In the present embodiment, by comparing the IMFs of FIG. 3B with the ultrasound image of FIG. 3A, a position and a size of a blood vessel on the ultrasound image and a flow rate of blood in the blood vessel are identified. In an actual application, the probe of the ultrasound imaging system 100, for example, sends the ultrasound signal to the phantom from a left side of FIG. 3A to obtain an echo signal. Therefore, in FIG. 3B, each of the IMFs may generate a signal variation in different media and interfaces, for example, at places encircled by dot lines and regions enclosed by two straight dotted lines. The places encircled by the dot lines are images of the vessel wall of FIG. 3A, and the regions enclosed by the two straight dot lines are flowing regions of the blood in the blood vessel, where a width W1 represents a size of the blood vessel, and D1 represents a distance between the vessel wall and the phantom, i.e. a position of the blood vessel. Moreover, the flow rate of blood in the blood vessel can also be calculated according to the intensity of each IMFs in the region enclosed by the two straight dotted lines. In the present embodiment, the flow rate of blood is, for example, 2.0 milliliters per second (2.0 ml/s). Therefore, such method can be used to determine the positions and the sizes of shallow and deep blood vessels in real-time, and can be used to determine the flow rate of blood in different blood vessels, so as to distinguish the type of the blood vessel, such as artery, vein or microvessel.

Figure 4A:
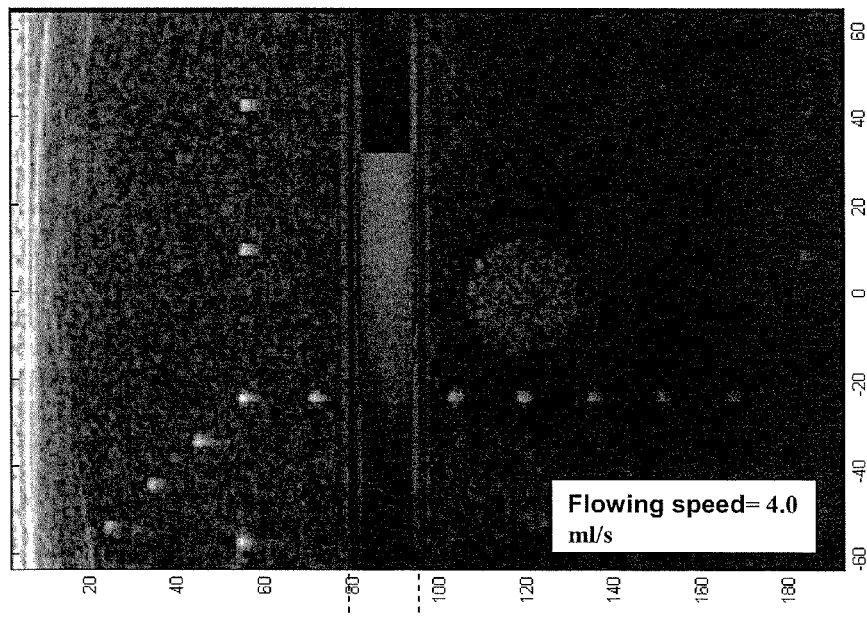
FIG. 4A is an ultrasound image of a phantom according to another embodiment of the disclosure.
Figure 4B:
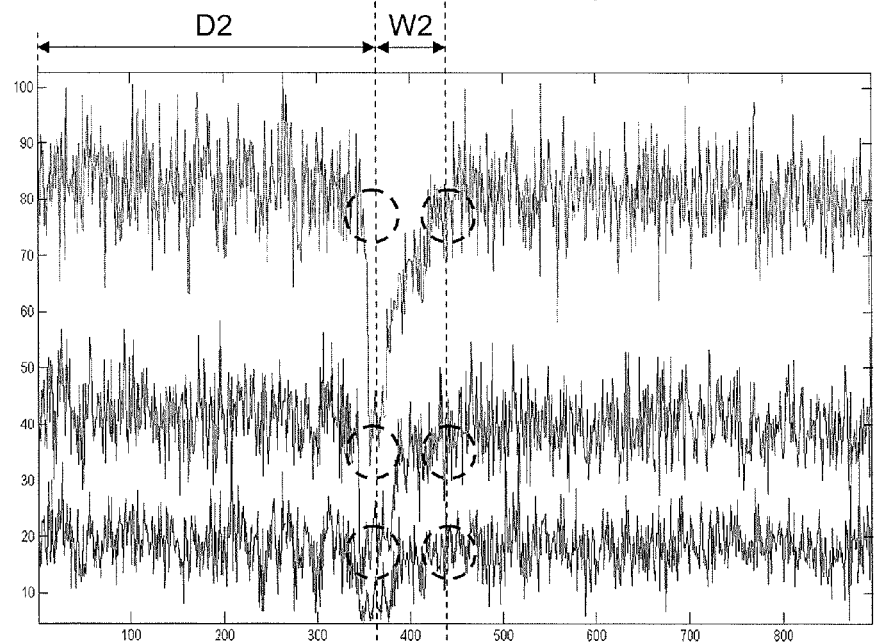
FIG. 4B is an IMF of a signal to be analyzed of the phantom of FIG. 4A.

FIG. 4A is an ultrasound image of a phantom according to another embodiment of the disclosure. FIG. 4B is an IMF of the signal to be analyzed of the phantom of FIG. 4A. The horizontal axis of FIG. 4A represents the depth of the phantom, and the vertical axis represents a position of the phantom. The horizontal axis of FIG. 4B represents the position of the phantom, and the vertical axis represents the normalized IMF intensity of each frequency band of the phantom. Referring to FIG. 4A and FIG. 4B, similarly, the IMFs of different frequency bands shown in FIG. 4B are IMFs obtained according to the signal analysis method of FIG. 1. In the present embodiment, by comparing (for example, by overlaying the plot of) the IMFs of FIG. 4B with the ultrasound image of FIG. 4A, the position and the size of a blood vessel on the ultrasound image and the flow rate of blood in the blood vessel are identified. In FIG. 4B, signal variations at places encircled by dotted lines are images of the vessel wall of FIG. 4A, and the regions enclosed by two straight dotted lines are flowing regions of the blood in the blood vessel, where a width W2 represents a size of the blood vessel, and D2 represents a distance between the vessel wall and the phantom, i.e. a position of the blood vessel. Moreover, by comparing the intensities of the IMFs in FIG. 3B and FIG. 4B, it is known that the intensities there between are different, which represents that flow rates of blood in the blood vessels of FIG. 3A and FIG. 4B are different. In the present embodiment, the flow rate of the blood in the blood vessel can be calculated according to the intensities of each IMFs in the region enclosed by the two straight dotted lines, and the flow rate of blood is, for example, 4.0 milliliters per second (4.0 ml/s).

In summary, in the exemplary embodiments of the disclosure, according to the signal analysis method, different characteristics of the signal in different media and interfaces are used to analyze frequency variations of the signal transmitted to different media and interfaces in collaboration of frequency band decomposition, so as to accurately describe a position and a size of the object to be detected. Moreover, the signal analysis method uses a phase processing means in collaboration with curve fitting to filter noises such as surges in the angular frequency information in time domain, so as to obtain stable angular frequency information, and learn an actual measurement circumstance of the region to be detected in real-time.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A time domain signal analysis method, comprising:
    receiving a signal to be analyzed;
    iteratively sifting the signal to be analyzed by using empirical mode decomposition (EMD) to extract at least one intrinsic mode function (IMF);
    performing a normalized Hilbert transform on the at least one IMF, wherein the transformed at least one IMF comprises phase information;
    processing the transformed at least one IMF by means of phase processing to obtain the at least one IMF comprising angular frequency information; and
    comparing the processed at least one IMF to a two-dimensional image related to the signal to be analyzed to identify image information of the two-dimensional image, wherein the image information of the two-dimensional image comprises a position, a size and a moving speed of a moving object.

2. The time domain signal analysis method as claimed in claim 1, wherein the step of processing the transformed at least one IMF by means of the phase processing is performed in a time domain.

3. The time domain signal analysis method as claimed in claim 1, wherein the step of processing the transformed at least one IMF by means of the phase processing comprises:
    taking the first order time derivative of the phase information of the at least one IMF to obtain the angular frequency information; and
    filtering a component of angular frequency beating information by means of curve fitting.

4. The time domain signal analysis method as claimed in claim 1, wherein the decomposed at least one IMF obtained in the step of iteratively sifting the signal to be analyzed by using the EMD comprises a plurality of IMFs of different frequency bands.

5. The time domain signal analysis method as claimed in claim 1, further comprising:
    sending a detecting signal to a region to be detected; and
    receiving the signal to be analyzed that is reflected by the region to be detected,
    wherein the two-dimensional image related to the signal to be analyzed comprises an image of the region to be detected.

6. The time domain signal analysis method as claimed in claim 5, wherein the region to be detected contains the moving object, and the signal to be analyzed that is reflected by the region to be detected comprises Doppler shift information of the moving object.

7. A method for analyzing an ultrasound image, adapted to an ultrasound imaging system, the method for analyzing the ultrasound image comprising:
    receiving a signal to be analyzed;
    iteratively sifting the signal to be analyzed by using empirical mode decomposition (EMD) to extract at least one intrinsic mode function (IMF);
    performing a normalized Hilbert transform on the at least one IMF, wherein the transformed at least one IMF comprises phase information;
    processing the transformed at least one IMF by means of phase processing to obtain the at least one IMF comprising angular frequency information; and
    comparing the processed at least one IMF to an ultrasound image related to the signal to be analyzed to identify image information of the ultrasound image,
    wherein the image information of the ultrasound image comprises a position, a size and a moving speed of a moving object.

8. The method for analyzing the ultrasound image as claimed in claim 7, wherein the step of processing the transformed at least one IMF by means of the phase processing is performed in time domain.

9. The method for analyzing the ultrasound image as claimed in claim 7, wherein the step of processing the transformed at least one IMF by means of the phase processing comprises:
    taking the first order time derivative of the phase information of the at least one IMF to obtain the angular frequency information; and
    filtering a component of angular frequency information by means of curve fitting.

10. The method for analyzing the ultrasound image as claimed in claim 7, wherein the decomposed at least one IMF obtained in the step of iteratively sifting the signal to be analyzed by using the EMD comprises a plurality of IMFs of different frequency bands.

11. The method for analyzing the ultrasound image as claimed in claim 7, further comprising:
    sending a detecting signal to a region to be detected; and
    receiving the signal to be analyzed that is reflected by the region to be detected,
    wherein the ultrasound image related to the signal to be analyzed comprises an image of the region to be detected.

12. The method for analyzing the ultrasound image as claimed in claim 11, wherein the region to be detected contains the moving object, and the signal to be analyzed that is reflected by the region to be detected comprises Doppler shift information of the moving object.

13. The method for analyzing the ultrasound image as claimed in claim 7, wherein the signal to be analyzed is obtained by detecting the region to be detected under an A-scan mode or a B-scan mode.

14. An ultrasound imaging apparatus, comprising:
    a signal transceiving circuit, receiving a signal to be analyzed;
    a signal processing circuit, iteratively sifting the signal to be analyzed by using empirical mode decomposition (EMD) to extract at least one intrinsic mode function (IMF); performing a normalized Hilbert transform on the at least one IMF, wherein the transformed at least one IMF comprises phase information; processing the transformed at least one IMF by means of phase processing to obtain the at least one IMF comprising angular frequency information; and comparing the processed at least one IMF to an ultrasound image related to the signal to be analyzed to identify image information of the ultrasound image, wherein the image information of the ultrasound image comprises a position, a size and a moving speed of a moving object; and an image display circuit, displaying the ultrasound image corresponding to a region to be detected according to a processing result of the signal to be analyzed that is processed by the signal processing circuit.

15. The ultrasound imaging apparatus as claimed in claim 14, wherein the signal processing circuit processes the transformed at least one IMF by means of the phase processing in a time domain.

16. The ultrasound imaging apparatus as claimed in claim 14, wherein when the signal processing circuit processes the transformed at least one IMF by means of the phase processing, the signal processing circuit takes the first order time derivative of the phase information of the at least one IMF to obtain the angular frequency information, and filters a component of angular frequency information by means of curve fitting.

17. The ultrasound imaging apparatus as claimed in claim 14, wherein the decomposed at least one IMF obtained by the signal processing circuit comprises a plurality of IMFs of different frequency bands.

18. The ultrasound imaging apparatus as claimed in claim 14, wherein the signal transceiving circuit sends a detecting signal to the region to be detected, and receives the signal to be analyzed that is reflected by the region to be detected, wherein the ultrasound image related to the signal to be analyzed comprises an image of the region to be detected.

19. The ultrasound imaging apparatus as claimed in claim 18, wherein the region to be detected contains the moving object, and the signal to be analyzed that is reflected by the region to be detected comprises Doppler shift information of the moving object.

20. The ultrasound imaging apparatus as claimed in claim 14, wherein the signal to be analyzed is obtained by the ultrasound imaging apparatus by detecting the region to be detected under an A-scan mode or a B-scan mode.

* * * * *